United States Patent [19]
Gardiner et al.

[11] Patent Number: 5,879,371
[45] Date of Patent: Mar. 9, 1999

[54] FERRULED LOOP SURGICAL FASTENERS, INSTRUMENTS, AND METHODS FOR MINIMALLY INVASIVE VASCULAR AND ENDOSCOPIC SURGERY

[75] Inventors: Barry N. Gardiner, Orinda; Paul T. McDonald, Oakland; Richard D. Phipps, Morgan Hill, all of Calif.

[73] Assignee: Elective Vascular Interventions, Inc., Palo Alto, Calif.

[21] Appl. No.: 781,577

[22] Filed: Jan. 9, 1997

[51] Int. Cl.⁶ .................................................. A61B 17/04
[52] U.S. Cl. .................. 606/224; 606/144; 606/147; 606/232
[58] Field of Search .................... 606/144, 224, 606/147, 232

[56] References Cited

U.S. PATENT DOCUMENTS

| | | |
|---|---|---|
| 2,201,610 | 5/1940 | Dawson . |
| 2,413,142 | 12/1946 | Jones et al. . |
| 2,430,293 | 11/1947 | Howells ........................................ 1/47 |
| 3,082,426 | 3/1963 | Miles .......................................... 1/349 |
| 3,150,379 | 9/1964 | Brown ......................................... 1/349 |
| 3,570,497 | 3/1971 | Lemole . |
| 3,802,438 | 4/1974 | Wolvek . |
| 3,910,281 | 10/1975 | Kletschka . |
| 4,111,206 | 9/1978 | Vishnevsky et al. .................... 128/305 |
| 4,129,059 | 12/1978 | Van Eck ....................................... 85/49 |
| 4,465,071 | 8/1984 | Samuels et al. ......................... 128/335 |
| 4,470,533 | 9/1984 | Schuler ..................................... 227/19 |
| 4,586,503 | 5/1986 | Kirsch et al. ............................ 128/334 |
| 4,595,007 | 6/1986 | Mericle .................................... 128/334 |
| 4,890,615 | 1/1990 | Caspari et al. ........................... 606/146 |
| 4,923,461 | 5/1990 | Caspari et al. ........................... 606/146 |
| 4,929,240 | 5/1990 | Kirsch et al. ............................. 606/151 |
| 4,957,498 | 9/1990 | Caspari et al. ........................... 606/146 |
| 5,002,563 | 3/1991 | Pyka et al. . |
| 5,032,127 | 7/1991 | Frazee et al. ............................ 606/143 |
| 5,035,692 | 7/1991 | Lyon et al. ............................... 606/143 |
| 5,100,421 | 3/1992 | Christoudias . |
| 5,207,694 | 5/1993 | Broome . |
| 5,222,961 | 6/1993 | Nakao et al. ............................. 606/143 |
| 5,250,053 | 10/1993 | Snyder ..................................... 606/145 |
| 5,261,917 | 11/1993 | Hasson et al. . |
| 5,282,825 | 2/1994 | Muck et al. . |
| 5,366,459 | 11/1994 | Yoon ........................................ 606/151 |
| 5,366,479 | 11/1994 | McGarry et al. ........................ 606/219 |
| 5,403,331 | 4/1995 | Chesterfield . |
| 5,417,700 | 5/1995 | Egan . |
| 5,437,680 | 8/1995 | Yoon ........................................ 606/139 |
| 5,437,681 | 8/1995 | Meade et al. ............................ 606/145 |
| 5,445,167 | 8/1995 | Yoon et al. ............................... 128/898 |
| 5,496,334 | 3/1996 | Klundt et al. ............................ 606/145 |
| 5,571,119 | 11/1996 | Atala ........................................ 606/145 |
| 5,603,718 | 2/1997 | Xu ........................................... 606/145 |
| 5,630,540 | 5/1997 | Blewett ................................. 227/176.1 |

FOREIGN PATENT DOCUMENTS

| | | |
|---|---|---|
| 0 072 232 A2 | 2/1983 | European Pat. Off. ......... A61B 17/12 |
| 0 122 046 | 3/1983 | European Pat. Off. ......... A61B 17/12 |
| 0 130 037 A1 | 1/1985 | European Pat. Off. ......... A61B 17/08 |
| 0 598 529 | 5/1994 | European Pat. Off. ......... A61B 17/12 |

(List continued on next page.)

*Primary Examiner*—Gary Jackson
*Attorney, Agent, or Firm*—Fliesler, Dubb, Meyer & Lovejoy LLP

[57] ABSTRACT

A surgical fastener in the form of a ferruled loop, instrument and method are provided for constructing a graft to artery anastomosis and other soft tissue anastomoses, particularly by minimally invasive (or endoscopic) surgery. The ferruled loop fastener is comprised of a needle, a suture and a ferrule. The needle and suture member allow this fastener to be sewn through, for example, a graft and artery to be joined. The ferrule member allows a ferruled loop to be formed without knotting the suture member, and that serves as a suture stitch to fasten the graft and artery together. The instrument holds the needle and ferrule at its distal end, and controls in the handle allow manipulation of the needle and controllable application of the fastener. The method employs the ferruled loop and instruments to join soft tissues and to construct graft to artery anastomoses.

27 Claims, 8 Drawing Sheets

FOREIGN PATENT DOCUMENTS

| | | |
|---|---|---|
| 0 632 999 A1 | 1/1995 | European Pat. Off. ......... A61B 17/04 |
| 0 656 191 | 6/1995 | European Pat. Off. ...... A61B 17/128 |
| 0 687 446 A2 | 12/1995 | European Pat. Off. ......... A61B 17/04 |
| 0 705 568 A1 | 4/1996 | European Pat. Off. ......... A61B 17/04 |
| 0 705 569 A1 | 4/1996 | European Pat. Off. ......... A61B 17/04 |
| 377052 | 6/1923 | Germany . |
| 3504202 A1 | 8/1985 | Germany . |
| 0 7308322 | 11/1995 | Japan ............................ A61B 17/10 |
| 0 8836544 | 12/1996 | Japan ............................ A61B 17/72 |
| WO 90/06725 | 6/1990 | WIPO ........................... A61B 17/12 |
| WO 91/08708 | 6/1991 | WIPO ........................... A61B 17/00 |
| WO 92/22041 | 12/1992 | WIPO ............................. G06K 7/10 |
| WO 93/01750 | 2/1993 | WIPO ........................... A61B 17/04 |
| WO 97/12555 | 4/1997 | WIPO ........................... A61B 17/11 |

FERRULED LOOP SURGICAL FASTENERS, INSTRUMENTS, AND METHODS FOR MINIMALLY INVASIVE VASCULAR AND ENDOSCOPIC SURGERY

CROSS REFERENCE TO RELATED APPLICATIONS

The present application is related to the following United States Patent Applications, which applications are by the same inventors as the present invention, and which applications are incorporated by reference herein in their entirety:

U.S. patent application Ser. No. 08/781,578, entitled, "Pinned Retainer Surgical Fasteners, Instruments and Methods for Minimally Invasive Vascular and Endoscopic Surgery", filed on Jan. 9, 1997, and currently pending; and U.S. patent application Ser. No. 08/781,579, entitled, "Sutured Staple Surgical Fasteners, Instruments and Methods for Minimally Invasive Vascular and Endoscopic Surgery", filed on Jan. 9, 1997, and currently pending.

FIELD OF INVENTION

This invention relates to the field of devices, instruments and methods for arterial replacement or bypass grafting by minimally invasive (or endoscopic) peripheral vascular and cardiovascular surgery.

BACKGROUND OF THE INVENTION

Minimally invasive surgery has allowed physicians to carry out many surgical procedures with less pain and disability than conventional, open surgery. In performing minimally invasive surgery, the surgeon makes a number of small incisions through the body wall to obtain access to the tissues requiring treatment. Typically, a trochar, which is a pointed, piercing device, is delivered into the body with a cannula. After the trochar pierces the abdominal or thoracic wall, it is removed and the cannula is left with one end in the body cavity, where the operation is to take place, and the other end opening to the outside. A cannula has a small inside diameter, typically 5–10 millimeters, and sometimes up to as much as 20 millimeters. A number of such cannulas are inserted for any given operation.

A viewing instrument, typically including a miniaturized video camera, is inserted through one of these cannulas and a variety of surgical instruments and retractors are inserted through others. The image provided by the viewing device may be displayed on a video screen or television monitor, affording the surgeon enhanced visual control over the instruments. Because a commonly used viewing instrument is called an "endoscope," this type of surgery is often referred to as "endoscopic surgery." In the abdomen, endoscopic procedures are commonly referred to as laparoscopic surgery, and in the chest, as thoracoscopic surgery. Abdominal procedures may take place either inside the abdominal cavity (in the intraperitoneal space) or in a space created behind the abdominal cavity (in the retroperitoneal space). The retroperitoneal space is particularly useful for operations on the aorta and spine.

Minimally invasive surgery has virtually replaced open surgical techniques for operations such as cholecystectomy and anti-reflux surgery of the esophagus and stomach. This has not occurred in either peripheral vascular surgery or cardiovascular surgery. An important type of vascular surgery is to replace or bypass a diseased, occluded or injured artery. Arterial replacement or bypass grafting has been performed for many years using open surgical techniques and a variety of prosthetic grafts. These grafts are manufactured as fabrics (often from Dacron or Teflon) or are prepared as autografts (from the patient's own tissues) or heterografts (from the tissues of animals). A graft can be joined to the involved artery in a number of different positions, including end-to-end, end-to-side, and side-to-side. This attachment between artery and graft is known as an anastomosis. Constructing an arterial anastomosis is technically challenging for a surgeon in open surgical procedures, and is almost a technical impossibility using minimally invasive techniques.

Many factors contribute to the difficulty of performing arterial replacement or bypass grafting. See generally, Wylie, Edwin J. et al., Manual of Vascular Surgery, (Springer-Verlag New York), 1980. One such factor is that the tissues to be joined must be precisely aligned with respect to each other to ensure the integrity and patency of the anastomosis. If one of the tissues is affixed too close to its edge, the suture can rip through the tissue and impair both the tissue and the anastomosis. Conversely, if the tissues are joined too far from their edges, it can significantly narrow the size of the anastomosis. Another factor is that, even after the tissues are properly aligned, it is difficult and time consuming to pass the needle through the tissues, form the knot in the suture material, and ensure that the suture material does not become tangled. These difficulties are exacerbated by the small size of the artery and graft. The arteries subject to peripheral vascular and cardiovascular surgery typically range in diameter from several millimeters to several centimeters. A graft is typically about the same size as the artery to which it is being attached. Another factor contributing to the difficulty of such procedures is the limited time available to complete the procedure. The time the surgeon has to complete an arterial replacement or bypass graft is limited because there is no blood flowing through the artery while the procedure is being done. If blood flow is not promptly restored, sometimes in as little as thirty minutes, the tissue the artery supplies may experience significant damage, or even death (tissue necrosis). In addition, arterial replacement or bypass grafting is made more difficult by the need to accurately place and space many sutures to achieve a permanent hemostatic seal. Precise placement and spacing of sutures is also required to achieve an anastomosis with long-term patency.

Highly trained and experienced surgeons are able to perform arterial replacement and bypass grafting in open surgery using conventional sutures and suturing techniques. A suture has a suture needle that is attached or "swedged on" to a long, trailing suture material. The needle must be precisely controlled and accurately placed through both graft and artery. The trailing suture material must be held with proper tension to keep the graft and artery together, and must be carefully manipulated to prevent the suture material from tangling. In open surgery, these maneuvers can usually be accomplished within the necessary time frame, thus avoiding the subsequent tissue damage (or tissue death) that can result from prolonged occlusion of arterial blood flow.

The difficulty of suturing a graft to an artery using minimally invasive surgical techniques has effectively prevented the safe use of this technology in both peripheral vascular and cardiovascular surgical procedures. When a minimally invasive procedure is done in the abdominal cavity, the retroperitoneal space, or chest, the space in which the operation is performed is more limited, and the exposure to the involved organs is more restricted, than with open surgery. Moreover, in a minimally invasive procedure, the instruments used to assist with the operation are passed into the surgical field through cannulas. When manipulating instruments through cannulas, it is extremely difficult to position tissues in their proper alignment with respect to each other, pass a needle through the tissues, form a knot in the suture material once the tissues are aligned, and prevent the suture material from becoming tangled. Therefore, although there have been isolated reports of vascular anastomoses being formed by minimally invasive surgery, no system has been provided for wide-spread surgical use which would allow such procedures to be performed safely within the prescribed time limits.

As explained above, anastomoses are commonly formed in open surgery by suturing together the tissues to be joined. However, one known system for applying a clip around tissues to be joined in an anastomosis is disclosed in a brochure entitled, "VCS Clip Applier System", published in 1995 by Auto Suture Company, a Division of U.S. Surgical Corporation. A clip is applied by an applying instrument about the tissues in a nonpenetrating manner, i.e., the clip does not penetrate through the tissues, but rather is clamped down around the tissues. As previously explained, it is imperative in forming an anastomosis that tissues to be joined are properly aligned with respect to each other. The disclosed VCS clip applier has no means for positioning tissues. Before the clip can be applied, the tissues must first be grasped and properly positioned with respect to each other, for example by skewering the tissues with a needle as in common suturing techniques and/or with forceps to bring the tissues together. As discussed, it is extremely difficult to perform such positioning techniques in minimally invasive procedures. Therefore, there is currently a need for a system adapted for wide-spread surgical use that is capable of manipulating and positioning tissues in a desired alignment with respect to each other, and thereafter capable of forming an anastomosis in minimally invasive procedures.

SUMMARY OF THE INVENTION

In view of the foregoing, it is an advantage of the invention to provide surgical fasteners that permit surgeons to perform peripheral vascular and cardiovascular surgery with minimally invasive techniques.

It is an advantage of the invention to provide surgical fasteners useful in minimally invasive procedures to replace or bypass a diseased, occluded or injured artery quickly, safely, and reliably.

It is an advantage of the invention to provide surgical fasteners useful in constructing an artery to graft anastomosis in the abdominal cavity, retroperitoneal space or chest.

It is an advantage of the invention to provide instruments and methods for precisely manipulating the fasteners and for applying the fasteners by minimally invasive surgery.

It is an advantage of the invention to provide fasteners, instruments and methods that permit surgeons to perform minimally invasive surgery by employing many of the same suturing skills and techniques they use in open surgery.

It is an advantage of the invention to provide surgical fasteners and instruments to hold them. Such fasteners and instruments enable other soft tissue anastomoses to be constructed and tissues to be joined together in the chest, retroperitoneum, or abdomen by minimally invasive techniques.

It is an advantage of the invention to provide surgical fasteners and instruments that are also capable of performing these procedures during traditional open surgery.

These and other advantages are achieved by providing a surgical fastener in the form of a ferruled loop, and an instrument for applying this fastener. The fastener has a needle, a suture material, and a ferrule. The fastener of the invention is designed to permit surgeons to construct vascular anastomoses, other soft tissue anastomoses, and to join together other soft tissues by minimally invasive surgery. The present invention provides these advantages while employing many of the same skills and techniques that are applicable to manipulating conventional sutures and suture needles and to constructing such anastomoses with conventional sutures. The needle is joined to one end of the suture material, and the ferrule is joined to the other end. The instrument of the invention has a handle at one end containing the controls and is attached by an elongated hollow shaft to the distal end of the instrument that contains a plurality of jaws. One jaw holds the needle, and another jaw holds the ferrule in a retracted position back inside the hollow shaft and out of view of the surgeon. The needle is used to pierce appropriate portions of a graft and artery with the sewing techniques surgeons commonly use. After the graft and artery have been pierced by the needle, the surgeon advances the ferrule out of its stored position inside the hollow shaft of the applying instrument, pushes the ferrule distally, applies the ferrule over the needle and pulls the needle (and the suture material) through the ferrule. This forms a loop in the suture material containing the graft and artery. The surgeon continues to pull the suture material through the ferrule so that the loop has the proper tension. This forms a closed ferruled loop in the suture material that serves as a "stitch" or "suture." The ferrule is then deformed to secure the loop. The excess suture from the needle end is then cut and removed with the needle. The ferruled loop fastener, together with the apparatus and methods to use it, permit an anastomosis between a graft and an artery using minimally invasive techniques.

While the invention is designed primarily for minimally invasive arterial grafting, the invention is also useful for attaching together a variety of other non-vascular soft tissues in the chest, retroperitoneal space or abdomen by minimally invasive techniques. For example, the invention may be used to construct an anastomosis in the stomach, intestine, or colon, or to perform any of the standard anti-reflux operations involving the stomach, esophagus, or diaphragmatic hiatus. The ferruled loop fasteners and instruments of the invention may also be used in an open surgical procedure.

BRIEF DESCRIPTION OF THE DRAWINGS

The above and other advantages of the present invention will be apparent upon consideration of the following detailed description, taken in conjunction with the accompanying drawings, in which like reference characters refer to like parts throughout, and in which.

DETAILED DESCRIPTION OF THE INVENTION

Embodiments of the present invention relate to a ferruled loop surgical fastener for fastening together an artery and a graft, and methods and apparatus for applying the fastener. In a preferred embodiment of the present invention, the fastener may be applied in a minimally invasive surgical procedure. However, it is also contemplated that the present invention may be used in open surgical procedures, utilizing suturing techniques commonly applied in open surgical procedures. It is also contemplated that the present invention may be used in open surgical procedures. As explained in greater detail below, the ferruled loop surgical fastener according to the present invention may be applied by a hand-held instrument manually or automatedly controlled by a surgeon, or alternatively, the fastener may be applied by a remotely controlled robotic mechanism. Furthermore, although a preferred embodiment of the invention is used to fasten together a vascular artery and a graft, it is understood that the present invention may be used to fasten together tissues, or a tissue and graft, in any surgical procedure where tissues or tissue and graft are to be fastened together.

Figures 1A, 1C:
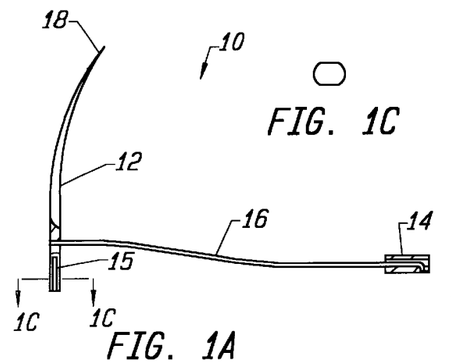
FIGS. 1A–C show, respectively, an illustrative embodiment of a ferruled loop surgical fastener in accordance with the invention, an alternative embodiment of such a fastener, and a cross-sectional view of the base portion of a needle of the fastener of FIGS. 1A and 1B, respectively.

Referring now to FIG. 1A, there is shown a ferruled loop surgical fastener 10 in general comprising a needle 12, a suture material 16, and a ferrule 14. The needle 12 is preferably biocompatible, and includes a tip 18 and a base 15 opposite tip 18. The needle 12 is designed so that tip 18 can pierce or penetrate a vascular graft and an artery, or any other tissues that are to be joined together, and allow the pierced graft, artery or other tissues to be placed onto the suture material 16. As explained hereinafter, the needle 12 is gripped by a fastener applying instrument permitting a surgeon to controllably join the graft and the artery with the same sewing motion that is used in open surgery.

As in needles used in conventional surgery, the needle 12 may be provided with a wide range of shapes, from straight to highly curved, and a variety of different sizes. Such needles are known in the art. Similarly, tip 18 of needle 12 may be formed of various configurations. In preferred embodiments of the invention, the needle is preferably provided with substantially the same range of piercing points, curvatures, and sizes as commercially available suture needles used with sizes 2-0 to 8-0 sutures. This range of piercing points, shapes, and sizes permits the surgeon to use essentially the same suturing (or sewing) motions that are currently used with conventional suture needles in open surgical procedures, and allows this invention to be used in a wide range of tissue fastening applications. The precise configuration of the needle may vary, depending on for example, the anatomy of the patient, the geometry of the surgical set-up, the area of the body in which the fasteners are to be applied, and the nature, type, and thickness of the tissues that are being joined together. As used herein, the term "tissue" may refer to any vascular passage or other body organ, and the term "graft" may refer to any biological or synthetic graft.

The needle must also be strong enough to withstand the forces encountered as the needle is driven through the tissues or graft. The needle is adapted to pierce or otherwise penetrate the structures to be joined. The tip 18 of the needle is shaped into a point designed to penetrate tissues without injuring, tearing, or otherwise affecting the integrity of the tissue. This is largely accomplished by forming tip 18 with a substantially circular, elliptical, or oblong cross-section, substantially free of a cutting edge. It is understood, however, that needle 12 may have a tip with a cutting edge along its length in alternative embodiments of the invention. Tip 18 of needle 12 may either taper to a point or have a blunt end, depending, for example, on whether the needle is passing through a normal and relatively undiseased artery, a calcified or artrosclerotic artery, or a thinned out, endarterectomized artery. A blunt tip needle may be preferable for use where a surgeon first needs to make a hole in the artery (or other tissue) with a punch. A blunt tip needle could then penetrate through this pre-punched hole. Such a procedure may be preferable in cases involving a severely calcified artery.

The base 15 of needle 12 is preferably configured to be releasably held by the distal tip of a manual or automated fastener applying instrument, explained in greater detail below. This allows the needle to be controlled during its penetration through the graft, the artery, or other tissues. The base 15 of the needle may have at least one slot, groove, or hole having a flat portion (shown in FIG. 1C) to permit the needle to be securely held by a distal tip of the applying instrument. The flat surface prevents the needle from rotating during use.

Figure 1B:
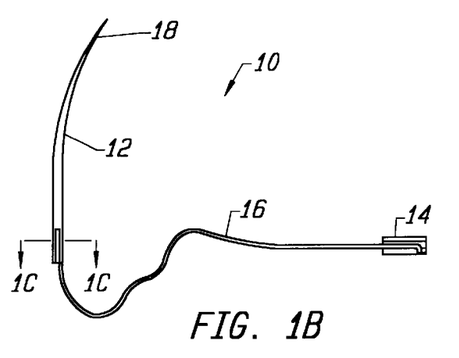

Suture material 16 is preferably any conventional type of suture material used in surgical procedures, including monofilament and polyfilament synthetic and natural materials. In a preferred embodiment, the suture material may be a monofilament wire made of a suitable biocompatible metal having a caliber substantially the same as that of the needle. A first end of the suture material 16 may be attached to the needle 12 adjacent to base 15 by techniques used to secure conventional suture materials to conventional suture needles, such as by swedging the suture material onto the needle. Suture material 16 may be joined to the needle 12 so that the suture material projects from the side of the needle (as shown in FIG. 1A), or the suture material may project from the end of the needle (as shown in FIG. 1B). In a preferred embodiment, suture material 16 may have a length ranging between 1 centimeter and 25 centimeters, and optimally between 2 centimeters and 10 centimeters. This length may vary in alternative embodiments of the invention.

An end of suture material 16 opposite that attached to needle 12 is attached to the ferrule 14. The ferrule 14 is adapted to engage and secure a portion of the suture material by the ferrule being crimped or otherwise deformed into pressure contact with the suture material, without cutting or substantially impairing the strength or integrity of the suture material. As shown in FIGS. 1A and 1B, in an embodiment of the invention, the suture material 16 may be attached to the ferrule 14, as for example by swedging or crimping, such that a length of the suture material adjacent the connection point passes through the ferrule. However, it is understood that the suture material 16 may be affixed to the ferrule 14 by different affixing techniques, and at different locations on the ferrule. Preferably, the ferrule is made of a non-absorbable, biocompatible metal, such as for example stainless steel, tungsten, or titanium. The ferrule may alternatively be made of a non-absorbable plastic, such as for example, teflon or nylon, or biodegradable polymers, such as polyglycolic acid. In alternative embodiments of the invention, an absorbable ferrule may be used if appropriate to the clinical situation (such as in joining certain soft tissues together temporarily or constructing anastomoses in the stomach, intestine, or colon). Both the ferrule and the suture may be formed of a bioabsorbable material for such applications.

Figure 2A:
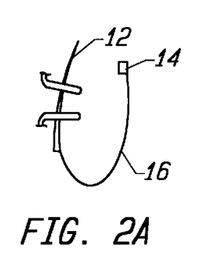
FIGS. 2A–F show an illustrative sequence of steps in applying the fasteners of FIGS. 1A and 1B.
Figure 2B:
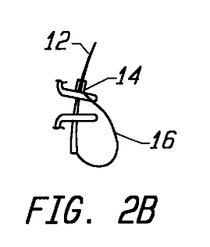
Figure 2C:
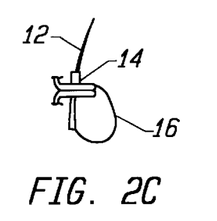
Figure 2D:
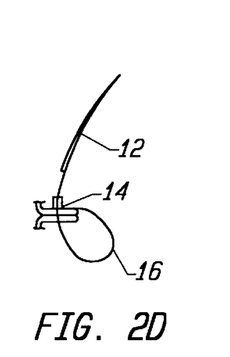
Figures 2E, 2F:
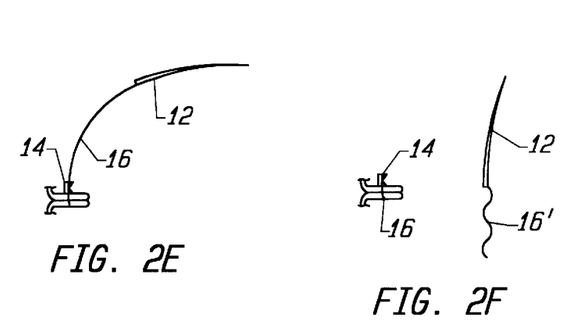

An illustrative sequence of steps for applying the ferruled loop surgical fastener 10 is shown in FIGS. 2A–F. In general, a surgeon may join a graft and artery together by using needle 12 and suture material 16 to sew the tissues together using conventional techniques. However, rather than knotting or tying the suture material 16 to form a stitch, the surgeon employs ferrule 14 to form a fastener securing portions of the graft and artery together. Referring now to FIG. 2A, the graft and artery to be joined are initially skewered onto needle 12. Ferrule 14 is next placed over the tip of the needle as shown in FIG. 2B, and pushed down on the needle, bringing the graft and artery together as shown in FIG. 2C. The needle 12 is next pulled through the graft, artery, and ferrule 14, forming a loop in the suture material 16 as shown in FIG. 2D. The needle 12 is next pulled to close the loop with an appropriate tension for fastening the graft and artery as shown in FIG. 2E. The ferrule 14 is then crimped or otherwise deformed to grip the suture material 16 so that the fastener according to the present invention is formed as shown in FIG. 2E. Suture material 16 may then be cut so that the needle 12 and excess suture material 16' may be removed. Accordingly, the ferruled loop surgical fastener of the present invention provides a knotless suture that may be used in place of a conventional interrupted suture.

Figure 3:
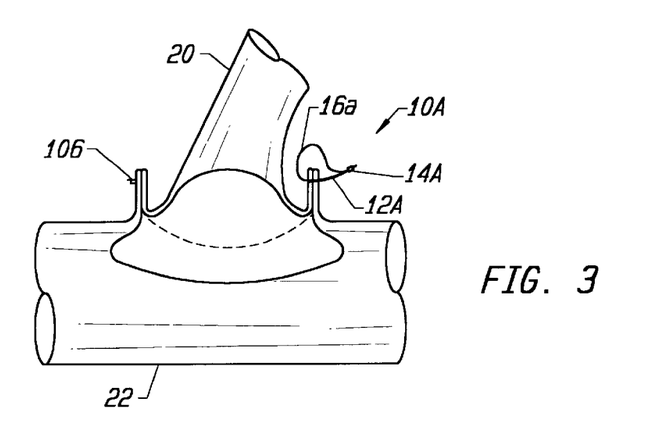
FIG. 3 shows an exemplary vascular anastomosis using a plurality of fasteners in accordance with the present invention.
Figure 4A:
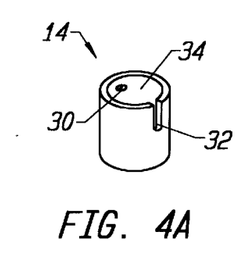
FIGS. 4A–C show an oblique view of an exemplary ferrule of the fastener of FIGS. 1A and 1B, a cross-sectional view of this ferrule, and a cross-sectional view of an alternative embodiment of such a ferrule, respectively.
Figure 4B:
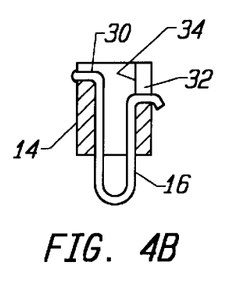
Figure 4C:
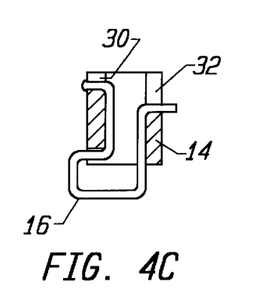

An illustrated use of the ferruled loop surgical fastener 10 in accordance with embodiments of the present invention is shown in FIG. 3. A graft 20 is joined to an artery 22 using fasteners 10a and 10b. A needle 12a of fastener 10a is first used to pierce graft 20 and artery 22 near the site of the anastomosis. Ferrule 14a is then placed onto needle 12a, creating a loop of suture material 16a to hold graft 20 to artery 22. The ferrule 14 is then crimped, the suture material is cut, and the excess suture material and needle are removed, thus providing a complete fastener such as fasteners 10a and 10b in FIG. 3. A plurality of such fasteners may be used to secure the graft 20 and the artery 22 together with a hemostatic seal.

In a preferred embodiment, the fastener 10 is a vascular fastener, and most preferably an arterial fastener. However, it is contemplated that the fastener according to the present invention may be used to attach a variety of non-vascular soft tissues together, such as for example in the abdominal cavity, the retroperitoneal space or in the chest. In each case, the soft tissues to be joined together are skewered onto the needle and a fastener is formed of the suture material and ferrule.

Several illustrative embodiments of the ferrule 14 are shown in FIGS. 4–7. In a preferred embodiment, ferrule 14 may be a generally tubular structure with round, oval, or square walls defining a central aperture, as shown in FIGS. 4A, 5A, 6A, and 6B, respectively. The aperture is sufficiently large to allow the needle and suture material to pass therethrough, so that the ferrule may be crimped or otherwise deformed to engage a portion of the suture material and prevent any significant movement of the ferrule with respect to the suture material. As shown in FIG. 4A, ferrule 14 may include a hole 30 formed in the wall to which the end of suture material 16 is secured. Once the tissues are supported within a loop of suture material 16, the end of suture material 16 affixed to needle 12 may be threaded through slot 32, as shown in FIGS. 4B and 4C, and the walls of the ferrule thereafter crimped to grip the suture material. An inner surface 34 of the walls of the ferrule 14 may have a roughened surface or may include circumferential grooves or ridges to enhance the grip on suture material 16.

Figure 5A:
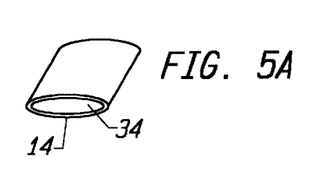
FIGS. 5A–C are perspective views of an alternative ferrule of a ferruled loop fastener.
Figure 5B:
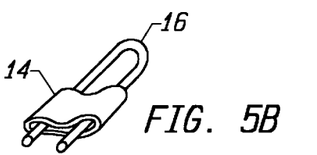
Figure 5C:
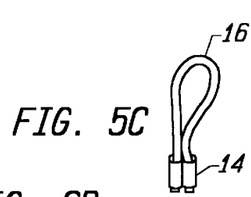
Figure 6A:
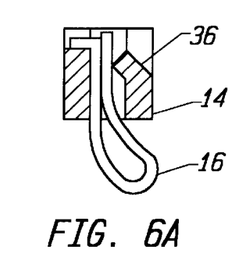
FIGS. 6A and 6B are, respectively, a side view, in section, and a plan view of another alternative ferruled loop fastener.
Figure 6B:
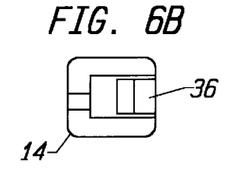
Figure 7A:
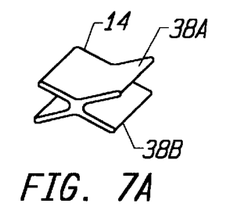
FIGS. 7A and 7B are perspective views of another alternative ferruled loop fastener.
Figure 7B:
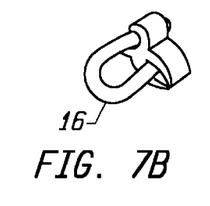

While the ferrule has thus far been described as a generally tubular structure, it is understood that the ferrule may be formed of other shapes, such as shown in FIGS. 5A–7B. As shown in FIGS. 5A–5C, the ferrule may be a partially deformed cylinder that is crimped to grip one end of the suture, and crimped to grip the other end. As shown in FIGS. 6A and 6B, the ferrule 14 may have an opening with a pre-formed tang 36, that is crimped inwardly to engage suture material 16. As shown in FIGS. 7A and 7B, the ferrule 14 may have an "X"-shaped cross-section, in which facing legs 38a and 38b may be crimped together to secure suture material 16. It is understood that the ferrule may have a variety of other shapes and sizes. It is further understood that various other clamping mechanisms and clips may be used instead of ferrule 14 in alternative embodiments of the invention. In its preferred embodiment, the opening in the ferrule that receives the needle has a funnel shaped configuration to guide the needle into and through the ferrule. It is also contemplated that the upper portion of the ferrule, i.e., the portion of the ferrule through which the needle first enters, may have an enlarged diameter relative to the remainder of the ferrule. In this way, the needle may be more easily guided into the ferrule.

In an alternative embodiment of the present invention, the ferrule may be omitted, and a preformed knotted loop in the suture material, such as for example a "fisherman's knot", may be provided. After the needle has skewered the tissues to be joined, the needle and leading portion of the suture material may be passed through the knotted loop. As is known in the art of knot tying, such a knotted loop may be provided such that, after the needle and leading portion of the suture material have passed therethrough, the knotted loop may be collapsed about the suture material by pulling the suture material taut, to thereby secure the suture material around the tissues with a desired tension. In such an embodiment, the ferrule holder member, described hereinafter, may be replaced by a member designed to hold and position the knotted loop in the proper orientation for receiving the needle and suture material therethrough.

Figure 8A:
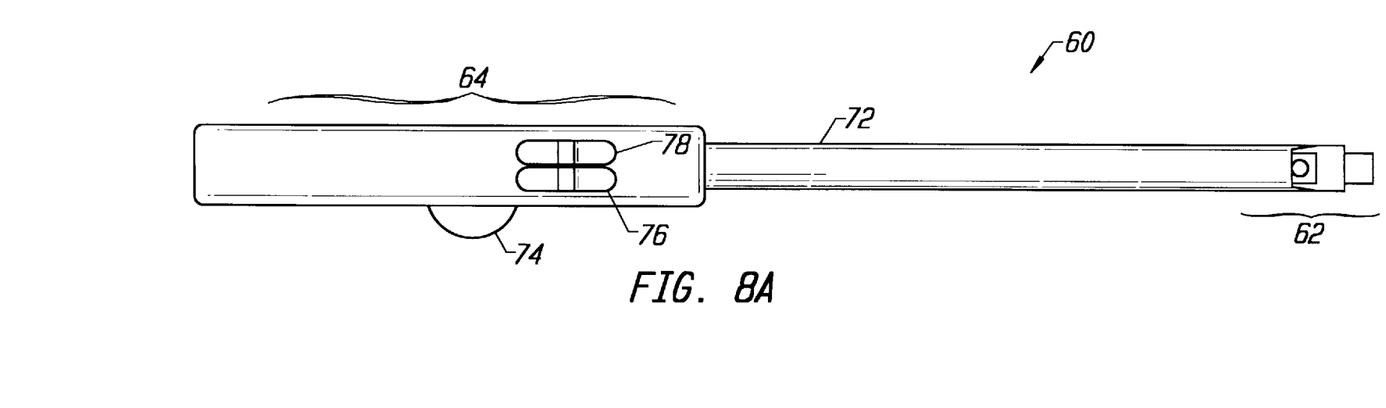
FIGS. 8A and 8B are, respectively, plan and elevation views of an illustrative embodiment of an applying instrument according to the present invention.
Figure 8B:
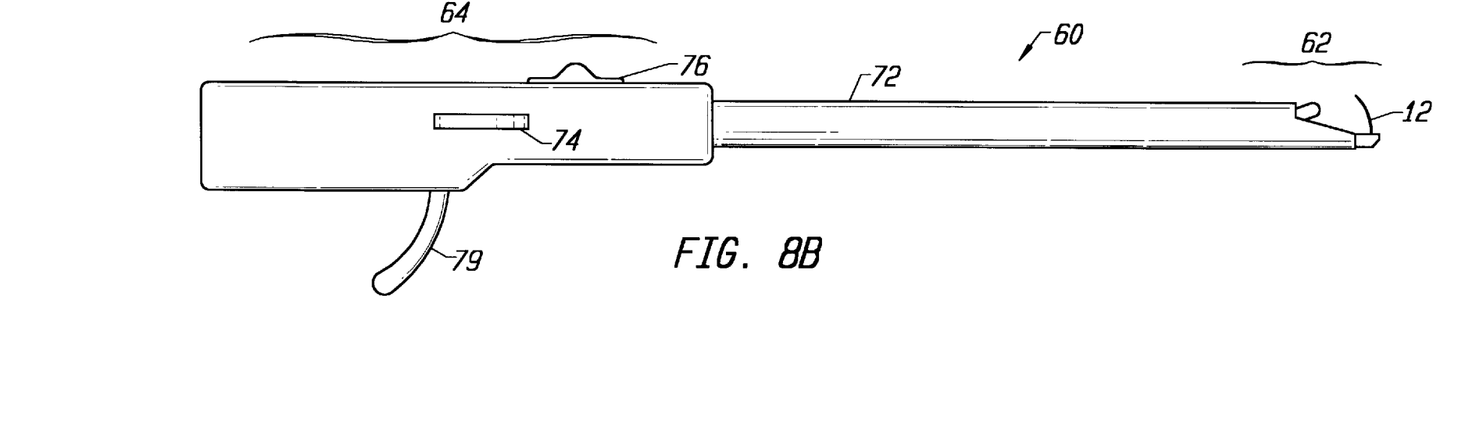

In addition to the ferruled loop surgical fastener described above, embodiments of the present invention also include an instrument for applying the ferruled loop fastener, in either minimally invasive or open surgical procedures. Referring now to FIGS. 8A and 8B, a ferruled loop applying instrument 60 is shown having a distal or working end 62, a proximal or handle end 64, and a shaft 72 between the proximal and distal ends. As explained hereinafter with respect to FIGS. 9A–12, working end 62 includes a needle holder member 102, a ferrule member assembly 110 (FIG. 11), a deforming member 140, and a needle pulling assembly 160 (FIG. 12), which components and assemblies cooperate together to apply the ferruled loop fastener 10. As further explained hereinafter with reference to FIGS. 9A–12, the handle end 64 includes control mechanisms for controlling the operation of the needle holder member 102, the ferrule member assembly 110, the deforming member 140, and the needle pulling assembly 160.

Shaft 72 may be either straight or curved, and is preferably made of a suitable rigid material, such as stainless steel, reinforced plastics, or composite materials, so that a surgeon may precisely control the working end of the instrument during surgery. Preferably, shaft 72 is about 5–10 millimeters in diameter so that it fits through and may be used with conventional canulas, but it may be as large as about 20 millimeters in diameter. Shaft 72 may have a variety of lengths suitable to particular surgical situations, and is preferably about 15–20 centimeters long. The shaft houses drive rods which couple the various controls on handle end 64 with the above-named components in working end 62, thus permitting the ferruled loop fastener to be manipulated and formed. The particular size, diameter, length and configuration of the instrument may vary depending on the size and shape of the needle, the geometry of the tissues to be joined or the artery to be grafted, anatomic variations, and the size of the surgical space and structures on which the surgeon is operating.

Figures 10A, 10B:
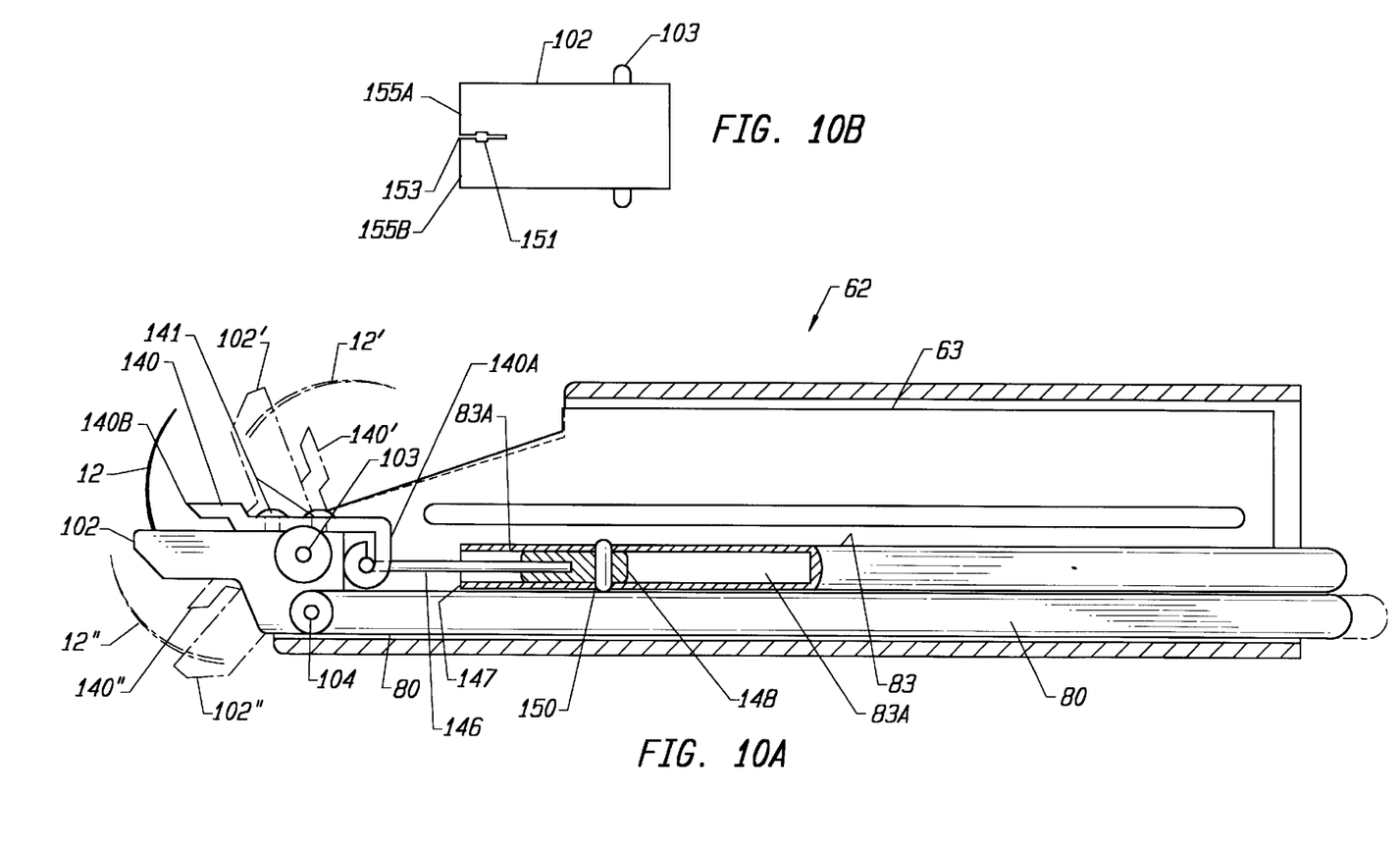
FIG. 10A is an elevation view, in section, of the working end of the applying instrument showing the needle holder assembly.
FIG. 10B is a plan view of the needle holder member shown in FIG. 10A.

Referring now to FIGS. 8A and 10A, needle holder member 102 in distal end 62 is provided for firmly but releasably gripping base 15 of needle 12, and for pivoting needle 12 with one degree of freedom relative to the shaft 72 (as indicated by the positions of the needle at 12, 12', and 12" in FIG. 10A). In a preferred embodiment, the needle holder member may articulate through at least about 90° of arc. However, specific surgical procedures may employ either larger or smaller ranges of motion. The elongated shaft of the instrument also allows the surgeon to rotate the instrument about the longitudinal axis of the instrument. These features provide the surgeon with a wide range of freedom to orient the needle relative to the tissues to be penetrated and joined together.

Needle holder member 102 may be articulated as follows. As shown on FIGS. 8A, 8B, and 9A, the handle end 64 includes a thumbwheel 74 for controlled manual rotation by a surgeon. Thumbwheel 74 is mounted on axle 88 with pinion 86 so that rotation of thumbwheel 74 causes an equivalent rotation of pinion 86. A rack gear 90 is coupled to drive rod 80, and is juxtaposed between various guides (not shown) so that teeth on rack gear 90 matingly engage with teeth on pinion 86. This rack and pinion assembly converts rotational movement of thumbwheel 74 into longitudinal motion of drive rod 80.

Drive rod 80 is pivotally mounted to needle holder member 102 by a pin 104 (FIG. 10A). Needle holder member 102 is in turn pivotally mounted on an axle 103, thus allowing needle holder member 102 to pivot with respect to shaft 72 about axle 103. As would be appreciated by those skilled in the art, rotation of thumbwheel 74 resulting in a proximal (i.e., rightward with respect to the views shown in FIGS. 9A and 10A) motion of drive rod 80 will cause a corresponding counterclockwise rotation of needle holder member 102 and needle 12 about axle 103 with respect to the view shown in FIG. 10A. Such movement of thumbwheel 74 may be used to move the needle holder member 102 and needle 12, for example, from their home position shown in solid in FIG. 10A to positions 102" and 12", respectively, shown in phantom in FIG. 10A. Conversely, rotation of thumbwheel 74 which results in a distal (i.e., leftward with respect to the views shown in FIGS. 9A and 10A) motion of drive rod 80 will cause a corresponding clockwise rotation of needle holder member 102 and needle 12 about axle 103 with respect to the view shown in FIG. 10A. Such rotation of thumbwheel 74 may be used to rotate, for example, needle holder member 102 and needle 12 from their home position as shown in FIG. 10A to their positions at 102' and 12' shown in phantom.

In operation, prior to insertion of the instrument to the surgical site, base 15 of needle 12 is inserted into a hole, or recess, 151 (FIG. 10B) in needle holder member 102. Hole 151 has a shape corresponding to the base portion of needle 12 shown in cross-section in FIG. 1C. Preferably, there is a sufficiently tight fit between base 15 and hole 151 to hold needle 12 securely in place. Alternatively, needle holder member 102 may be partially split by slot 153, as shown in FIG. 10B, in which case hole 151 is preferably slightly smaller than the size of base 15 of needle 12. Thus, insertion of base 15 into hole 151 spreads arms 155a and 155b slightly apart, thereby providing a secure hold on needle 12.

When a surgeon is inserting instrument 60 into a patient, thumbwheel 74 is manipulated to pivot needle holder member 102 and needle 12 to a closed position at 102' and 12', respectively, so that needle 12 will not interfere with passing working end 62 through a canula to the surgical site. After insertion, a surgeon may manipulate thumbwheel 74 to pivot needle holder member 102 and needle 12 as required. For example, a surgeon may pivot needle holder member 102 to a fully open position 102" to skewer a graft, and then return the needle holder member to a home position 102 or a closed position 102' to prevent the graft from falling off while the graft is positioned adjacent to an artery. Subsequently, thumbwheel 74 may again be manipulated to position needle holder member 102 at open position 102" so that the needle 12 can skewer the artery to be joined with the graft. In some cases, a surgeon may wish to fix the position of needle 12 with respect to working end 62. Various known mechanisms (not shown) such as thumbwheel detents or adjustable drag devices, as well as drive rod clamps and the like may be provided for this purpose. While manipulating tissue, various forces are applied to needle 12. Needle holder member 102 must be capable of maintaining the needle 12 in a fixed position as selected by the surgeon.

Figure 9A:
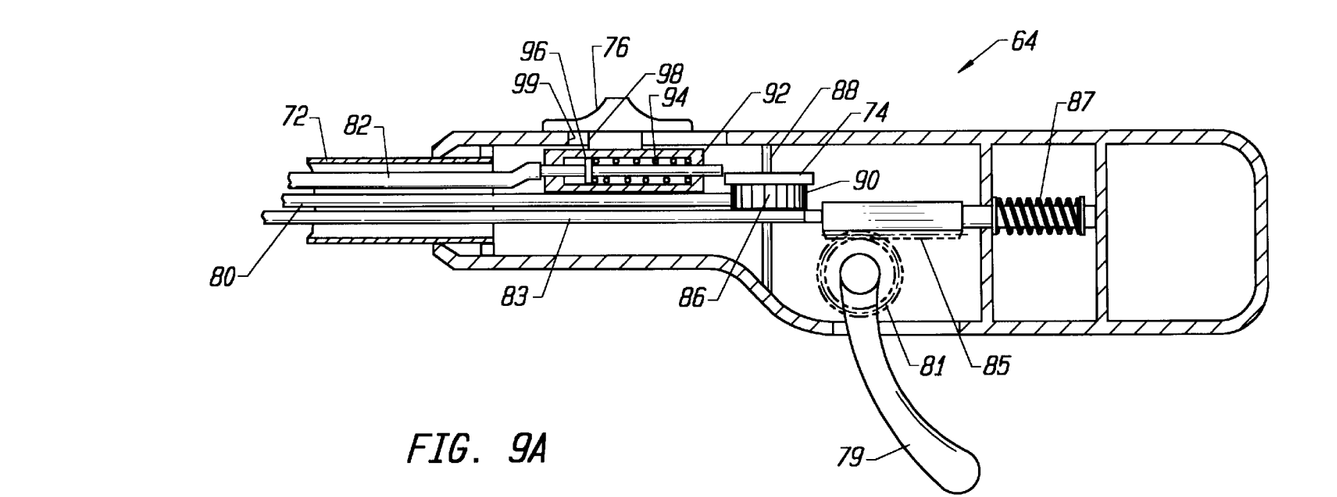
FIGS. 9A and 9B are, respectively, elevation views, partially in section, of the handle and working end of the applying instrument.
Figure 9B:
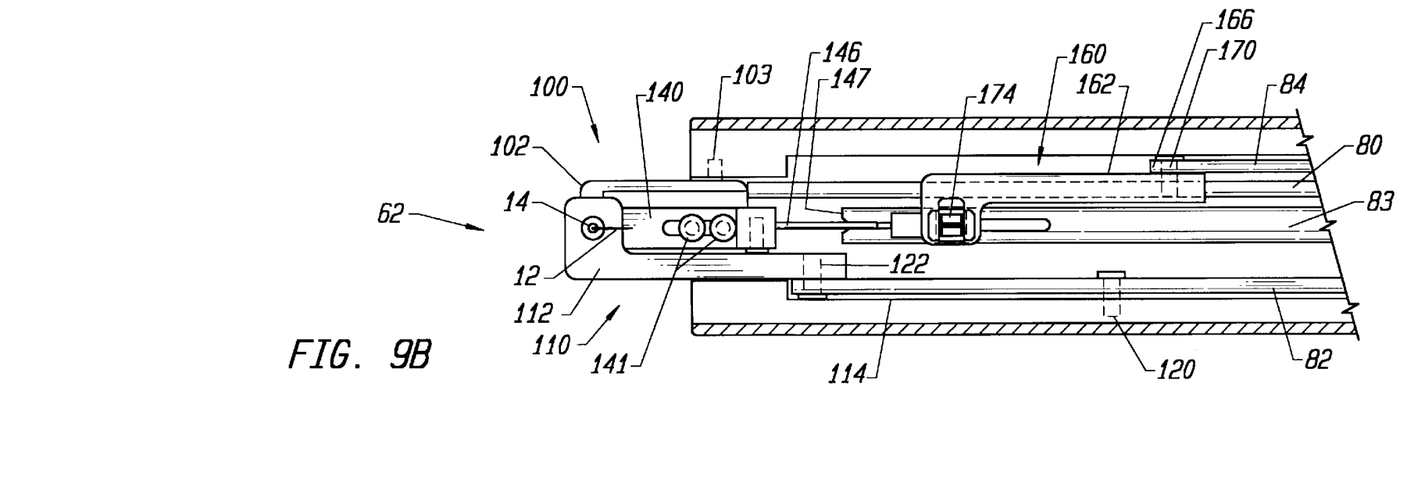
Figure 11:
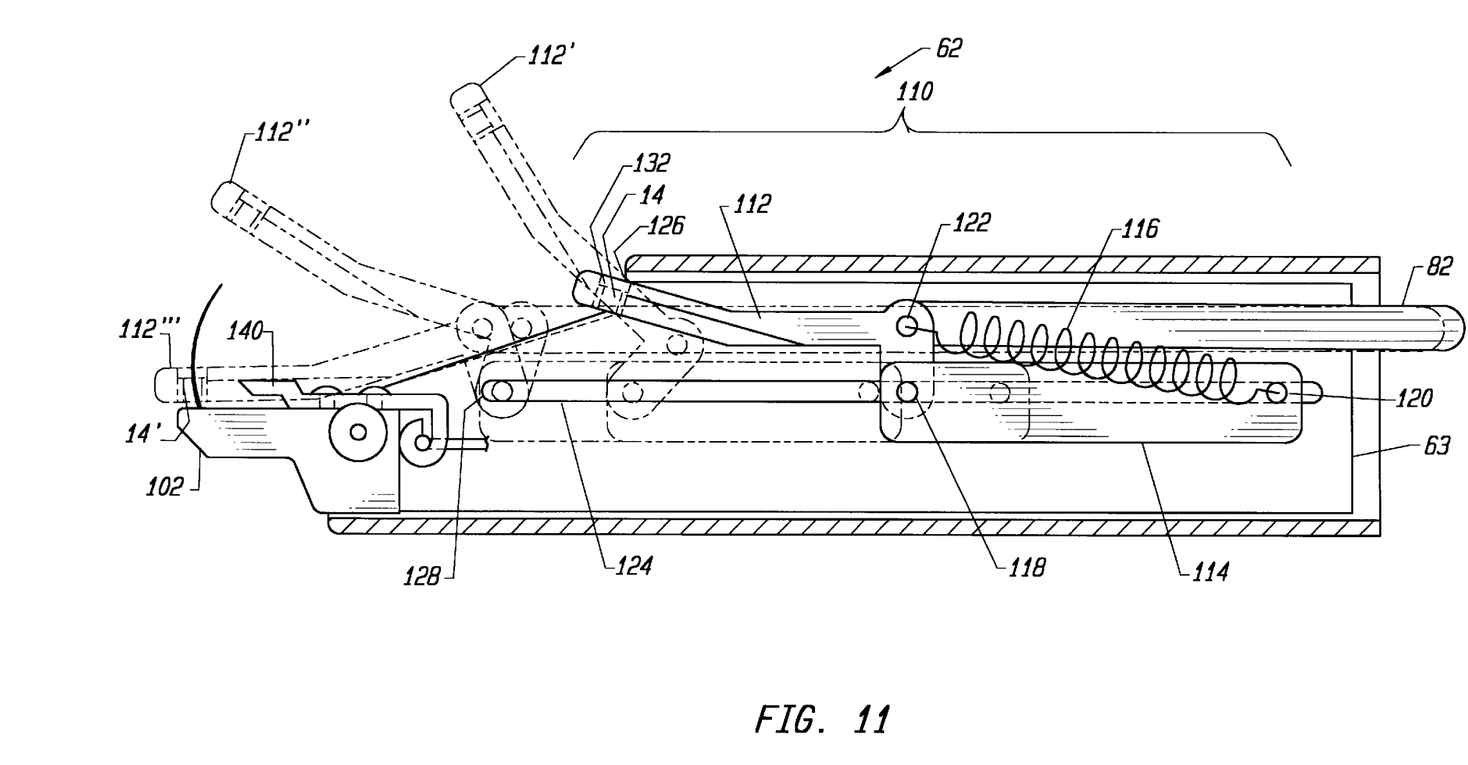
FIG. 11 is an elevation view, in section, of the working end of the applying instrument showing the ferrule holder member and related assembly.

As shown in FIGS. 9B and 11, working end 62 further includes ferrule member assembly 110. In general, ferrule member assembly 110 is provided to support a ferrule 14 while tissues are being skewered by the needle 12, and to subsequently position the ferrule 14 over the needle 12. The ferrule member assembly 110 is connected to drive rod 82, which is in turn connected to a slide 76 in handle end 64, as shown in FIGS. 8A, 8B, and 9A. During use of the instrument 60, it may be possible that the ferrule member assembly becomes bound, or otherwise prevented from moving, as for example if a ferrule and needle are not correctly aligned with each other upon an attempt to locate the ferrule on the needle. Therefore, in a preferred embodiment, a force limiter may be provided between the slide 76 and the drive rod 82 so that, if the drive rod is bound or prevented from moving, the force limiter limits the force exerted on drive rod 82.

The force limiter is comprised of a housing 92, a spring 94 and a pin, or washer, 96. Slide 76 is fixedly mounted with respect to housing 92 such that translation of slide 76 within slot 99 will cause a one-to-one translation of housing 92. Spring 94 is mounted within housing 92, with a first end abutting against the rear of the housing 92 and a second end abutting against washer 96. The washer 96 is fixedly mounted on drive rod 82. With this configuration, a distal movement (i.e., to the left in FIG. 9A) of the slide 76 and housing 92 will either: 1) move the spring 94 and drive rod 82 distally (where the shaft is not bound or otherwise prevented from moving); or 2) compress the spring 94 between the rear of housing 92 and the washer 96 (where the drive rod is bound or prevented from moving). In this way, slide 76 may be actuated to move drive rod 82 distally where drive rod 82 is free to move, but, where drive rod is bound, a distal movement of slide 76 will not forcibly move rod 82, which forced movement could otherwise damage the rod 82, the ferrule member assembly 110 and/or needle 12. It is understood that the slide 76 may be coupled directly to the drive rod 82 in alternative embodiments of the invention.

Referring to FIGS. 9B and 11, ferrule member assembly 110 in working end 62 of the instrument includes ferrule holder member 112, carriage 114, and spring 116. Ferrule holder member 112 is pivotally attached to drive rod 82 at a pin 122, and ferrule holder member 112 is also pivotally attached to a first point on carriage 114 by a pin 118. Ferrule holder member 112 is additionally coupled to a second point on carriage 114 via spring 116 attached between pin 122 and a pin 120. Spring 116 biases carriage 114 distally with respect to ferrule holder member 112. Additionally, as ferrule holder member 112 is mounted to carriage 114 at pin 118, spring 116 biases ferrule holder member 112 to rotate clockwise about pin 122. Working end 62 further includes a support member 63 having a slot 124 formed therein. Pins 118 and 120 of the carriage 114 are mounted and ride within slot 124 such that carriage 114 is free to translate distally until pin 118 abuts against end 128 of slot 124.

In FIG. 11, ferrule holder member 112 and carriage 114 are shown in solid in their retracted position. This position is used when inserting working end 62 to the surgical site and while manipulating and skewering the tissues, or graft and tissue. The retracted position of the ferrule holder member within the shaft 72 provides a clear line of sight to the needle and needle holder by the surgeon. When the tissues are in proper position, the needle holder member 102 is returned to its home position. The home position is the position of needle 12 and needle holder member 102 required for applying ferrule 14 to needle 12. Preferably, this position may be positively identified by a detent mechanism on thumbwheel 74. In its retracted position, a top portion of ferrule holder member 112 lies in contact with an edge 126 of working end 62. In order to locate a ferrule 14 on top of needle 12, slide 76 is actuated to move drive rod 82 distally. Distal movement of drive rod 82 moves ferrule holder member 112 distally, which in turn moves carriage 114 distally. Once ferrule holder member 112 clears the edge 126, the biasing force of spring 116 moves carriage 114 distally with respect to ferrule holder member 112, and rotates ferrule holder member 112 clockwise to a position of the ferrule holder member shown in phantom at 112'. Continued distal motion of drive rod 82 moves ferrule member assembly 110 until pin 118 contacts end 128 of slot 124. Further distal motion of drive rod 82 then causes counterclockwise rotation of the ferrule holder member 112 about pin 118.

A distal end of ferrule holder member 112 includes a hole, or bore, 132 for frictionally supporting ferrule 14. The counterclockwise rotation of ferrule holder member 112 causes ferrule 14 to be passed over tip 18 of needle 12. The funnel shaped opening on the interior surface of the ferrule helps guide needle 12 into and through the ferrule. Guided by visual indications, such as markings on the shaft of needle 12, and by tactile feedback to the drive rod 82 and slide 76, a surgeon continues to manipulate slide 76 until ferrule holder member is brought to a position 112''' and the ferrule is brought to a position 14'. In this position, the ferrule 14 is properly positioned with respect to the needle holder member 102, and the ferrule 14 is in a position where it may be acted upon by the deforming member 140 explained hereinafter.

Figure 12:
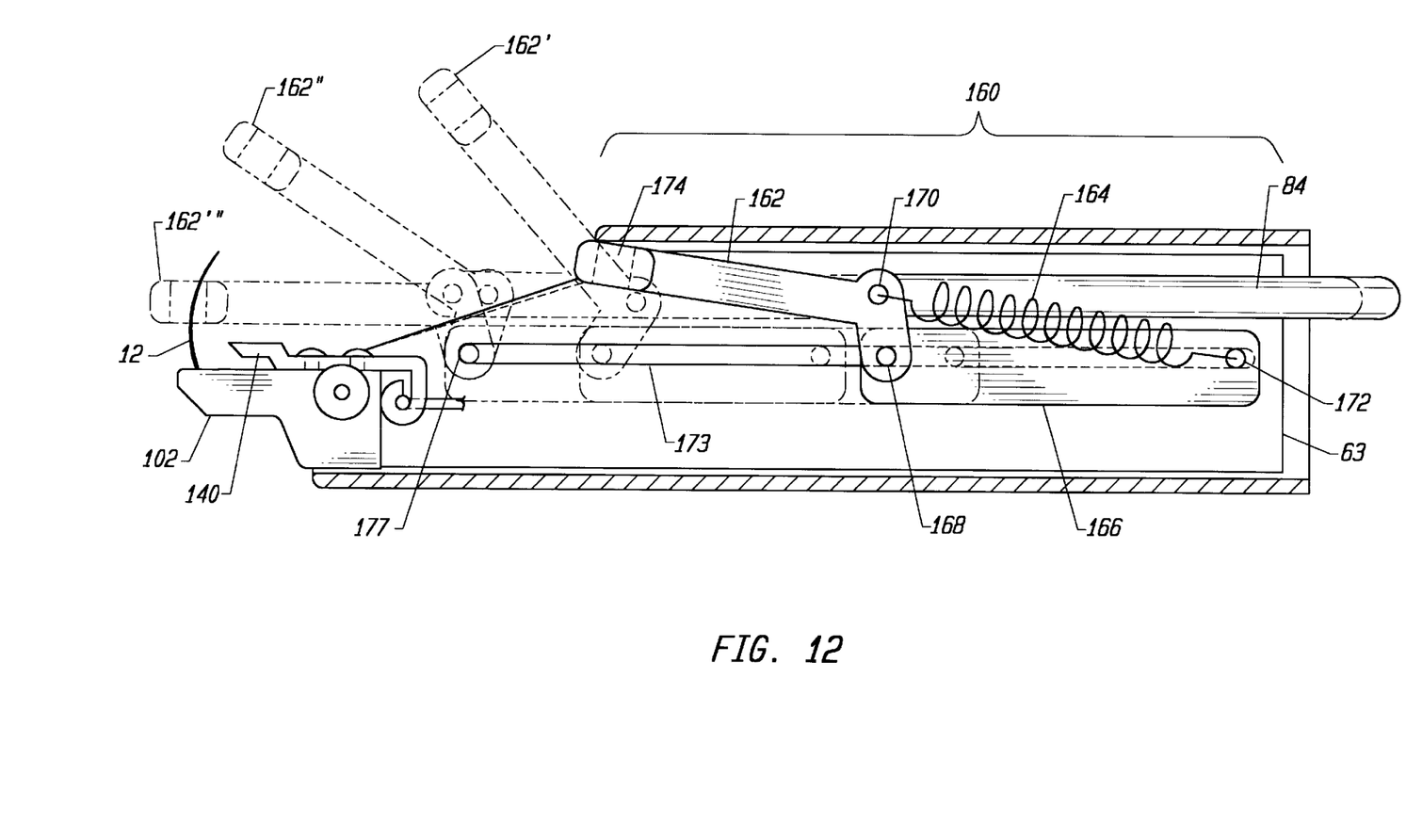
FIG. 12 is an elevation view, in section, of the working end of the applying instrument showing the needle pulling member and related assembly.

Working end 62 further includes a needle-pulling assembly 160, as shown in FIGS. 9B and 12. In general, needle-pulling assembly 160 grips needle 12 after ferrule 14 is in place thereon, and pulls needle 12 and a length of suture material 16 through ferrule 14 to form a tight loop around the tissues to be fastened together. Needle-pulling assembly 160 operates in substantially the same way as ferrule member assembly 110 described above. The ferrule member assembly 110 and the needle-pulling assembly 160 may be substantially structural mirror images of each other, with one assembly located on the right side of the instrument and the other assembly located on the left side of the instrument with respect to a top view of the instrument. In a preferred embodiment, both the ferrule holder assembly and the needle pulling assembly are stored out of the surgeon's line of sight proximally inside the hollow shaft 72 while the tissues are being skewered and positioned on the needle 12.

In a preferred embodiment, the ferrule 14 is held in place by the ferrule holder member 112 while the needle-pulling assembly 160 operates to pull the needle and suture material through the ferrule 14. However, it is understood that in alternative embodiments of the invention, the ferrule holder member 112 may have located the ferrule 14 over needle 12 and then returned to its retracted position prior to the needle-pulling assembly 160 pulling the needle and suture material through the ferrule. In this alternative embodiment, the ferrule deforming member 140 (explained hereinafter) may engage and hold the ferrule in place as the needle-pulling assembly pulls the needle and suture material through the ferrule.

The needle-pulling assembly 160 includes a needle pulling member 162, carriage 166 and spring 164 (FIG. 12). The needle-pulling assembly 160 is connected to drive rod 84, which is in turn connected to a slide 78 in handle end 64 (FIG. 8A). In a preferred embodiment, slide 78 is attached directly to drive rod 84. However, in an alternative embodiment of the invention, a force limiter as described above with respect to the handle mechanisms controlling the ferrule member assembly may be interposed between the slide 78 and the drive rod 84. Such a force limiter would allow slide 78 to be moved distally without forcing a corresponding distal movement of drive rod 84 in the event that drive rod 84 is bound or otherwise prevented from moving.

As shown in FIGS. 9B and 12, needle pulling member 162 is pivotally attached to drive rod 84 at a pin 170, and the needle pulling member 162 is pivotally attached to a first point on carriage 166 by a pin 168. Needle pulling member 162 is additionally attached to a second point on carriage 166 via spring 164 attached between pin 170 and a pin 172. Spring 164 biases carriage 166 distally with respect to the needle pulling member 162. Additionally, as the needle pulling member 162 is mounted to carriage 166 at pin 168, spring 164 biases needle pulling member 162 to rotate clockwise about pin 170. Support member 63 includes a second slot 173 on an opposite side of the instrument from slot 124 utilized in association with the ferrule member assembly. Pins 168 and 172 are mounted and ride within slot 173 such that carriage 166 is free to translate distally until pin 168 abuts against an end 177 of slot 173.

In FIG. 12, the needle pulling member 162 and carriage 166 are shown in solid in their retracted position inside shaft 72, and out of the surgeon's field of view of the surgical site. This position is maintained when inserting working end 62 to the surgical site and while manipulating and skewering the tissues. The needle pulling member 162 also remains in the retracted position while the ferrule member assembly is driven distally out of shaft 72 and while the assembly locates the ferrule 14 over needle 12. The ferrule holder member and ferrule are omitted from FIG. 12 for clarity. In its retracted position, a top portion of needle pulling member 162 lies in contact with edge 126 of working end 62. In order to locate needle pulling member 162 over needle 12, slide 78 is actuated to move drive rod 84 distally. Distal movement of drive rod 84 moves needle pulling member 162 distally, which in turn moves carriage 166 distally. Once needle pulling member 162 clears the edge 126, the biasing force of spring 164 moves carriage 166 distally with respect to the needle pulling member 162, and rotates the needle pulling member 162 clockwise to a position of the needle pulling member shown in phantom at 162'. Continued distal movement of drive rod 84 moves needle-pulling assembly 160 until pin 168 contacts the end 177 of slot 173. Further distal motion of drive rod 84 then causes rotation of the needle pulling member 162 about pin 168.

Figure 13A:
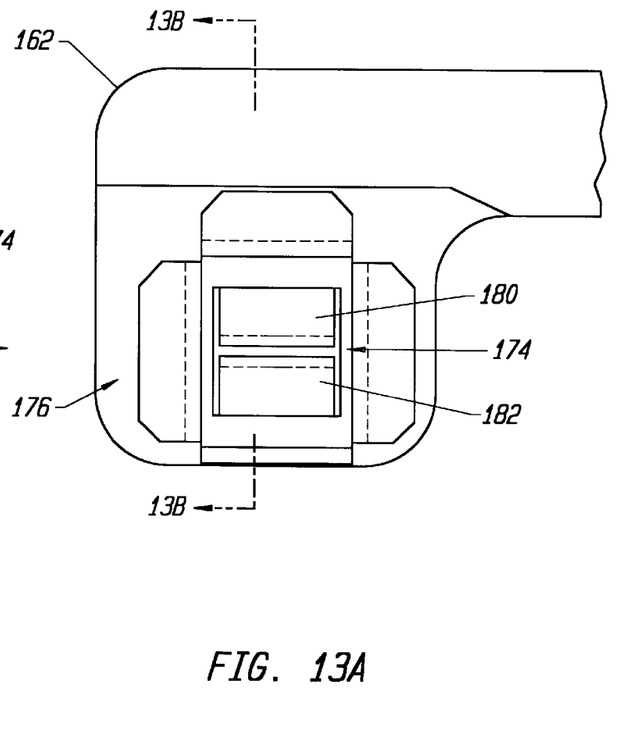
FIGS. 13A and 13B are, respectively, plan and elevation views of a gripper of the needle pulling member of FIG. 12.
Figure 13B:
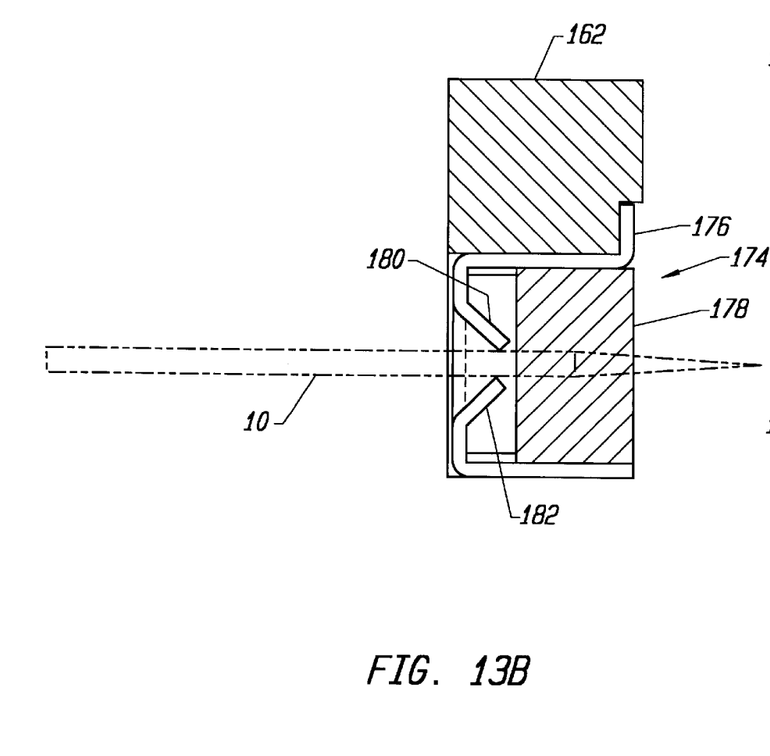

Needle pulling member 162 includes a gripper 174 (FIGS. 13A and 13B) which operates by allowing needle 12 to be easily inserted therein when needle pulling member 162 is advanced from position 162" to position 162'" (FIG. 12), but prevents needle 12 from being withdrawn therefrom when needle pulling member 162 is retracted in the opposite direction. As shown in FIGS. 13A and 13B, gripper 174 comprises two main components: self-energizing gripping member 176, and needle stabilizer 178. Gripping member 176 is typically made of a strong, hard metallic material, which would preferably be stainless steel. It is also preferable that the material of which gripping member 176 is made be harder than the material from which needle 12 is made. Gripping member 176 may be press-fit into a square hole formed in the needle-pulling assembly 160 and securely held therein. Needle stabilizer 178 is preferably made of an elastomeric material, such as silicone. Needle stabilizer 178 is shaped to fill the square hole in needle-pulling assembly 160 above gripping member 176. Gripping member 176 preferably has a funnel shaped opening similar to the ferrule to help guide needle 12 into the gripping member.

Gripping member 176 comprises two diagonally oriented (with respect to the base of gripping member 176) locking members 180 and 182. Needle-pulling assembly 160 is aligned with respect to needle 12 such that, as the needle pulling member 162 advances over needle 12, the needle 12 passes between the locking members 180 and 182 as shown in FIG. 13B. Upon the subsequent retraction of the needle-pulling assembly 160, needle 12 is trapped between the sharp edges of locking members 180 and 182 due to the force moments such contact induces in locking members 180 and 182. Specifically, the greater the extraction force upon needle 12, the greater the force moments induced in locking members 180 and 182. Sufficiently strong force moments will cause the sharp edges of locking members 180 and 182 to plastically deform needle 12 at their points of contact with needle 12. Such plastic deformation ensures a secure grip of locking members 180 and 182 on the needle 12. Upon being inserted into gripping member 176, needle 12 will also penetrate needle stabilizer 178. Needle stabilizer 178 prevents needle 12 from rotating substantially about its contacts with locking members 180 and 182. Thus, when needle pulling member 162 is retracted, needle 12 is pulled free from needle holder member 102, through the tissues being joined, and through the ferrule 14. Continued retraction of needle pulling member 162 also draws suture material 16 through the tissues and ferrule 14 to thereby tighten a suture stitch around the tissues. Controls for operating needle-pulling assembly 160 may be designed to prevent a surgeon from tightening a suture beyond a predetermined limit, such as by inclusion of a force limiting mechanism as described above. After the suture stitch is formed with an appropriate tension, as defined by a surgeon visually observing the tissue compression and tactile feedback provided by the control for the needle-pulling assembly, a deforming member may then be used to deform or crimp the ferrule as described below, to thereby secure the ferruled loop.

As shown in FIG. 10A, distal end 62 further includes a deforming member 140 translationally mounted to an upper surface of needle holder member 102. Deforming member 140 may be translationally mounted to needle holder member 102 by means of a slot formed within the deforming member which slidably engages rivet heads 141. As indicated on FIG. 10A, deforming member 140 remains stationary with respect to needle holder member 102 as needle holder member pivots about axle 103.

Deforming member 140 is coupled via flexible wire 146 and slide 148 (explained hereinafter) to drive rod 83, which drive rod 83 is in turn coupled to a lever 79 in the handle end 64 of the instrument (FIG. 9A). Lever 79 is mounted with pinion gear 81 on a common shaft. Drive rod 83 is affixed to a rack gear 85 which meshes with pinion gear 81. Thus, operation of lever 79 causes rotation of pinion gear 81 resulting in translation of drive rod 83. Spring 87 biases drive rod 83 in a proximal direction to maintain drive rod 83 in a proximal position absent actuation of lever 79.

Actuation of lever 79 moves drive rod 83 distally until an end 147 of drive rod 83 contacts a portion 140a of deforming member 140. Upon continued actuation of lever 79, end 147 of drive rod 83 moves deforming member 140 distally so that an end 140b of deforming member 140 contacts ferrule 14 to crimp or otherwise deform ferrule 14 into a pressure contact with the suture material 16. Lever 79 and associated components are preferably designed to transmit sufficient force to drive rod 83 to accomplish deformation of ferrule 14, and drive rod 83 must be capable of withstanding the resulting compressional loads.

The end of drive rod 83 includes a bore hole 83a in which is mounted a slide 148 attached to flexible wire 146, which wire 146 is in turn affixed to deforming member 140. Bore hole 83a further includes a slot (not shown) longitudinally formed through the outer wall of bore hole 83a. A pin 150 affixed to slide 148 rides within this slot. Upon releasing lever 79, spring 87 moves drive rod 83 proximally. Deforming member 140, wire 146 and slide 148 remain stationary during proximal movement of drive rod 83 until a distal edge of the slot contacts pin 150, whereupon pin 150, slide 148, wire 146 and deforming member 140 are pulled proximally with drive rod 83. The wire 146 and slide 148 allow deforming member 140 to pivot with needle holder member 102 without relative movement between the deforming member and needle holder member, and without exerting a force on drive rod 83 and lever 79. As would be appreciated by those skilled in the art, deforming member 140 may be attached to drive rod 83 by mechanisms other than wire 146 and slide 148 in alternative embodiments of the invention.

After the deforming member 140 has fastened the ferrule in proper position around the suture material, excess suture material may then be trimmed in a conventional manner, and the instrument, along with the needle 12 and excess suture material may then be withdrawn from the patient.

The instrument described above may be formed by constructing the controls in the handle end 64, attaching the drive rods to the controls at the handle end, and affixing the assemblies in the working end 62 to the drive rods and to the support member 63. Thereafter, the support member 63 may be inserted in the distal end of shaft 72 and affixed by suitable means. Alternatively, working end 62 may be designed to accept the various assemblies directly, without using support member 63.

Up to this point, the assemblies in the working end have been described as being actuated and controlled by manually operated thumbwheels and slides in the handle end of the instrument. However, in alternative embodiments of the invention, it is understood that formation of ferruled loop fastener, and its release from the applier may be automated by driving the drive rods and distal mechanisms of the instrument through their ranges of motion by motors, actuators, pneumatic or hydraulic systems, or some other force transmission mechanism instead of or in addition to the manual actuation of the drive rods and distal mechanisms as described above. In such an embodiment, the motors, actuators and/or other force transmission mechanisms may be activated by known, manually activated switches or buttons in the handle end of the instrument. As would be appreciated by those skilled in the art, actuation of the drive rods to affect the motions of the various assemblies in the working end as described above may be accomplished by affixing the proximal ends of the drive rods to the motors, actuators and/or force transmission mechanisms to bring about the desired controlled movement of the drive rods and working end assemblies and therefore automate these functions. Additionally, force limiters may be provided to limit the force with which the motors and/or actuators drive the drive rods and tube. The force limiters may be mechanical, such as of the type described above, or the force limiters may be electrical, such as closed loop feedback signals which monitor the amount of force exerted on the drive rods and/or distal end assemblies.

In a further embodiment of the present invention, it is contemplated that the manually operated mechanisms in the handle end may be omitted, and the assemblies in the working end of the instrument may be actuated and controlled by a surgical robot, to which shaft 72, and the assemblies and mechanisms contained therein, are attached. In such an embodiment, motors, actuators, pneumatic/hydraulic systems and/or other force transmission mechanisms may be provided as described above for driving the drive rods and assemblies in the working end of the instrument for forming and releasing a ferruled loop fastener. The motors, actuators and/or other force transmission mechanisms may in turn be controlled remotely by a computer and/or a surgeon.

The method uses the instrument of the invention containing at least one ferruled loop fastener, as described above. A small incision is made in the patient's abdomen, chest, or retroperitoneal space, depending on the clinical situation, and the distal end of the elongated shaft of the instrument is inserted through this opening. In carrying out a vascular anastomosis, the surgeon first inserts the piercing tip of the needle through the exterior wall of a vascular graft. The tip of the needle is then inserted through the interior lumen of the artery, and through the arterial wall at the appropriate location. If the artery is heavily calcified, the surgeon may make a hole in the artery, using a punch or other device, before inserting a blunt tipped needle through the arterial wall. Once the needle is in place (through both the graft and the arterial wall), the surgeon operates the instrument to move the ferrule over the needle. The surgeon then moves the needle pulling member over the needle and retracts this member to pull the needle and the suture member through the graft, the arterial wall and the ferrule. Further movement allows tightening of the stitch with proper tension. The ferrule is then deformed or crimped through use of appropriate instrument controls, to secure the closed ferruled loop and secure the graft and the arterial wall together. The excess suture material is cut and needle and excess suture material withdrawn. Preferably, this method results in the anastomotic edges of the graft and artery being substantially everted. Preferably, this procedure isolates the intra-luminal area from coming in contact with the fastener.

The method may involve repeating these steps to apply a series of additional fasteners. These steps are repeated with additional fasteners being applied around the anastomotic lumen, until the artery and graft have been joined together in a substantially hemostatic relationship. The method may also be used in conjunction with other fasteners, or with conventional suturing, to provide a hemostatic anastomosis. This method is useful in end-to-end, side-to-end, and side-to-side procedures. In the construction of a vascular anastomosis, these fasteners are applied at positions and locations identical to those used for conventional sutures, and suturing techniques. Hence, the fasteners may be applied to within about 0.5 millimeters to about 5 millimeters from the cut edge of the arterial wall, and within no less than 3 threads of the cut end of a prosthetic, woven graft, as the absolute minimum. The number of fasteners will vary with the size of the artery and the circumference of the anastomosis. The instrument of the invention allows the surgeon to use essentially similar techniques as those employed by surgeons to manipulate suture needles through tissues and grafts in traditional open surgery.

The method of vascular grafting using this present invention may be illustrated in the context of an endoscopic aortobifemoral bypass procedure. The patient is positioned on the operating room table midway between a right lateral decubitus position and a supine position, resulting in availability of the left flank and both groins to be sterilely prepared for operation. The table is slightly flexed to open the iliac crest-costophrenic angle. A standard sterile preparation of the patient is performed. Standard draping technique is accomplished. Standard vertical groin incisions are made to mobilize the common femoral, superficial femoral, and profunda femoral arteries in each groin. By finger dissection, a tunnel toward the abdomen is made from each incision by palpation along the course of the common femoral artery just superior to the common femoral artery and just below the inguinal ligament. The tunnel is extended as far as a finger can palpate.

Along the mid axillary line as drawn to the iliac crest midway between the iliac crest and the ribs a small incision is made in the skin and subcutaneous tissue. Utilizing finger dissection, dissection is carried down through the fat to the posterior muscles. A balloon dissector is then placed through this small incision at this location and a cavity created. When the balloon dissector has created a cavity in the potential space between the retroperitoneal fat and the psoas muscle, then the cavity is further expanded by placing a sealed port and insufflating $CO_2$. Once insufflating has been accomplished, the space is examined and a correct relationship between the lateral and anterior abdominal walls is established so then in the centermost portion of the roof of the cavity a port is made to insert a lifting device. The dissection continues without further $CO_2$ insufflation.

Several small incisions are made in the abdominal wall to carefully position abdominal wall retractors which are attached to the lifting device. With the space now developed and the aorta exposed from the renal vein to the bifurcation and the left iliac artery exposed to the left hypogastric artery, further dissection is accomplished superiorly around the aorta and each of the lumbar vessels and also just above the right common iliac artery. Care is again taken to ensure not entering the peritoneal cavity. The aorta is completely dissected free just below the renal arteries which are identified visually, and each of the lumbar vessels is controlled with temporary clips. The quality of the pulse in the aorta is confirmed by comparison with preoperative angiograms to ensure that the correct area for anastomosis of the bypass graft has been obtained and that the aorta is soft and pliable and will accept surgical fasteners. Dissection is then completed to both groins and the tunnels that were started in each groin is noted to be complete by passing a tunneler from the groin along the previously palpated space of the iliac artery to the retroperitoneal cavity (created by the primary dissection of the aorta).

A correctly sized graft is then selected and fashioned to ensure that the bifurcation length is appropriate, and the proximal end is trimmed for either an end-to-end or end-to-side anastomosis. The graft is then introduced through a port into the dissected space and each of the limbs are appropriately positioned in the groins where they will ultimately be attached. An appropriate aortic clamp is selected to clamp the aorta just below the renal arteries, and another clamp is selected for clamping the aorta at the level of the inferior mesenteric artery. The aorta is cross-clamped. Ischemia time begins at this point and the operation is directed to be done as expeditiously as possible.

If an end-to-end anastomosis is planned, then the aorta is divided and excess aorta is removed to permit exposure of the end of the infra renal aorta. The graft which has been previously positioned is then held by graspers, and the system of the invention is utilized to attach the graft to the aorta. Each fastener is placed in turn at appropriate spacing to ensure correct sealing of the graft to the aorta. After all fasteners have been placed and secured, a clamp that may grasp either limb of the graft is applied to the limbs of the graft, and the aorta clamp is temporarily opened to distend the graft with normal pulsatile arterial flow. Upon noting a secure anastomosis, the proximal aortic clamp is removed, however if any leak points are noted another fastener is applied or sewn into place positioned to close the bleeding point.

When hemostasis is secure, the left limb of the graft is passed though the tunnel by grasping it with a grasper from the groin incision and the graft is delivered into the groin wound. A standard end of graft to side of common femoral or profunda femoris artery is performed. A similar process is utilized for the right groin. Each graft limb in turn is opened to flow upon satisfactory completion of the anastomosis. The fasteners are used to sew closed the stump of the distal aorta. Areas are inspected to ensure adequate hemostasis, and when this is ensured, wounds are irrigated with antibiotic solution. The retroperitoneal cavity is then allowed to collapse upon the newly placed graft. No closure of this cavity is required as the ports and laprolift are removed. Laparoscopic wounds are then closed in standard fashion ensuring absorbable sutures close the small fascial defects and the skin wounds are steri-stripped. The open groin wounds are then closed in standard fashion utilizing three layers for closure of each wound and the skin edges are approximated with staples.

It is to be understood that the embodiments shown as described above are only illustrative of the principles of the invention, and various modifications can be made by those skilled in the art without departing from the scope and spirit of the invention, such as joining together any two tissues present in the abdomen, chest, or retroperitoneum. The skilled artisan will also appreciate that the present invention can be practiced by other than the described embodiments, which are provided for purposes of illustration and not of limitation, and that the present invention is only limited by the claims that follow.

We claim:

1. A surgical fastener comprising:
   a suture material,
   a needle having a base portion joined to a first end of the suture material, said needle capable of skewering and aligning tissues, or tissue and graft, in an endoscopic procedure, and said needle capable of positioning the suture material around the tissues, or tissue and graft, and
   a ferrule joined to a second end of the suture material, said ferrule including an opening for receiving said needle and a length of said suture material therethrough, said ferrule capable of being deformed to engage said length of suture material to secure said suture material around the tissues, or tissue and graft.

2. A fastener defined in claim 1 wherein the base portion of the needle is configured to be releasably engaged with an associated applying instrument.

3. A surgical fastener comprising:
   a suture material,
   needle means joined to a first end of said suture material, said needle means capable of skewering and aligning tissues, or tissue and graft, in an endoscopic procedure, and said needle means capable of positioning the suture material around the tissues, or tissue and graft, and
   ferrule means joined to a second end of said suture material, said ferrule means including an opening for receiving said needle means and a length of said suture material therethrough, said ferrule means capable of engaging said length of suture material upon being deformed to secure said length of suture material in a fixed position with respect to said ferrule means.

4. A fastener defined in claim 3 wherein the needle means further comprises base means for releasably engaging an associated applying instrument.

5. An instrument for applying a surgical fastener comprising:
   an elongated shaft assembly having a distal end portion,
   a needle holder at the distal end portion for engaging a needle having a base portion joined to a first end of a suture material,
   a ferrule holder at the distal end portion for holding a ferrule joined to a second end of the suture material, and for placing the ferrule over the needle,
   a needle pulling member at the distal end portion for pulling the needle away from said needle holder to form a loop in the suture material,
   a deforming member at the distal end portion for securing the ferrule to a selected point on the suture material, and
   controls located remotely from the distal end portion for controlling operation of the ferrule holder, needle pulling member, and deforming member.

6. An instrument defined in claim 5 wherein the elongated shaft has a length and width adapted to use in minimally invasive surgery.

7. An instrument as defined in claim 5 wherein the needle holder is also adapted to articulate the needle relative to the elongated shaft, and the controls including means for articulating the needle holder.

8. An instrument as defined in claim 5 wherein the elongated shaft comprising at its distal end portion a needle and a ferrule has a maximum diameter less than about 20 millimeters.

9. An instrument for applying a surgical fastener as recited in claim 5, wherein said controls comprise hand-actuated controls.

10. An instrument for applying a surgical fastener as recited in claim 5, wherein said controls comprise automated robotic controls.

11. An instrument for applying a surgical fastener comprising:

an elongated shaft assembly having a distal end portion, needle means at the distal end portion for engaging a needle joined to a suture member, ferrule means at the distal end portion for engaging a ferrule also joined to the suture member and placing the ferrule over the needle, needle pulling means at the distal end portion for pulling the needle to form a loop in the suture member and to tighten the loop, deforming means at the distal end portion for securing the ferrule to a selected point on the suture member, and a handle having control means for actuating the ferrule means, the needle pulling means and the deforming means.

12. An instrument defined in claim 11 wherein the elongated shaft has a length and width adapted to use in minimally invasive surgery.

13. An instrument as defined in claim 11 wherein the needle means has means to articulate the needle relative to the elongated shaft, and the handle has control means for actuating such articulation means.

14. An instrument as defined in claim 13 wherein the elongated shaft comprising at its distal end portion a needle and a ferrule has a maximum diameter less than about 20 millimeters.

15. A method for attaching soft tissues located in the abdomen, chest and retroperitoneal space and for attaching a graft to an artery in these areas comprising:

providing an instrument for applying a surgical fastener having an elongated shaft with a distal end portion and having a ferrule holder member, a needle pulling member, and a deforming member at the distal end portion adapted to form a ferruled loop, providing to a needle holder member at the distal end portion, a needle comprising a suture needle having a base portion joined to a first end of a suture member, providing to the ferrule holder member, a ferrule joined to a second end of the suture member and adapted to engage and secure the suture at another selected point along its length, incising a patient's tissues to create at least one opening into the patient's abdominal cavity, chest or retroperitoneal space, inserting the distal end of the instrument through the opening, so that the distal end is disposed in the patient, passing the needle through a portion of one tissue, graft or artery and through a portion of a second tissue, artery or graft, and actuating the ferrule holder member, needle pulling member, and deforming member to form a closed ferruled loop containing a portion of one tissue, graft or artery and a portion of a second tissue, artery or graft.

16. The method defined in claim 15 wherein the passing and actuating steps are repeated to apply additional fasteners.

17. The method defined in claim 15 wherein the incising step creates a small incision and wherein the inserting, passing and actuating steps are performed by minimally invasive surgical procedures.

18. The method defined in claim 15 wherein the needle is passed through a portion of a graft or artery and through an artery or graft to form a portion of an artery to graft anastomosis.

19. The method defined in claim 15 wherein the artery is selected from the group consisting of the aorta, the coronary arteries, the iliac arteries and the femoral arteries.

20. The method defined in claim 19 wherein the artery is at least about 2 millimeters diameter or larger.

21. An instrument for applying a surgical fastener as recited in claim 5, further comprising connecting means for connecting said controls to said ferrule holder, said needle pulling member, and said deforming member.

22. An instrument for applying a surgical fastener as recited in claim 21, wherein said controls and said connecting means together comprise an automated robotic system for actuating said ferrule holder, said needle pulling member, and said deforming member.

23. An instrument for applying a surgical fastener as recited in claim 21, further comprising a motor, controlled by said controls, for actuating said connecting means.

24. An instrument for applying a surgical fastener as recited in claim 21, further comprising pneumatic means, controlled by said controls, for actuating said connecting means.

25. An instrument for applying a surgical fastener as recited in claim 21, further comprising hydraulic means, controlled by said controls, for actuating said connecting means.

26. A method of fastening together tissues, or tissue and graft, in a minimally invasive procedure, comprising the steps of:

(a) skewering the tissues, or tissue and graft, onto a needle having a trailing suture material attached thereto in a minimally invasive procedure;

(b) locating a ferrule attached to the suture material at an end of the suture material opposite the needle over the needle with a ferrule holder;

(c) grasping said needle with a needle pulling member;

(d) pulling said needle grasped in said step (b) through the ferrule to position the suture material around the tissues, or tissue and graft; and (e) deforming the ferrule with a ferrule deforming member to fix the suture material around the tissues, or tissue and graft.

27. A method of fastening together tissues, or tissue and graft, in a minimally invasive procedure as recited in claim 26, further comprising the step (f) of providing a clear line of sight for a surgeon to the needle during said step (a) by positioning the ferrule holder, the needle pulling member, and the deforming member out of the line of sight.

* * * * *